(12) United States Patent
Burnes et al.

(10) Patent No.: US 8,478,406 B2
(45) Date of Patent: Jul. 2, 2013

(54) APPARATUS AND METHODS OF DELIVERING AN ENHANCED REFRACTORY PERIOD STIMULATION THERAPY

(75) Inventors: John E. Burnes, Andover, MN (US); David E. Euler, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1901 days.

(21) Appl. No.: 11/379,886

(22) Filed: Apr. 24, 2006

(65) Prior Publication Data

US 2007/0250124 A1    Oct. 25, 2007

(51) Int. Cl.
*A61N 1/365* (2006.01)
(52) U.S. Cl.
USPC .................................. 607/17; 607/9
(58) Field of Classification Search
USPC ..................... 607/4, 6, 9, 14, 18, 19
See application file for complete search history.

(56) References Cited

U.S. PATENT DOCUMENTS

| 4,406,286 | A |   | 9/1983 | Stein |
| 4,821,724 | A | * | 4/1989 | Whigham et al. ............. 607/13 |
| 2002/0183686 | A1 |   | 12/2002 | Darvish et al. |
| 2003/0023279 | A1 |   | 1/2003 | Spinelli |
| 2003/0153957 | A1 | * | 8/2003 | Bradley .......................... 607/27 |
| 2004/0049235 | A1 |   | 3/2004 | Deno et al. |
| 2005/0021098 | A1 | * | 1/2005 | Spinelli et al. .................... 607/9 |
| 2005/0038479 | A1 | * | 2/2005 | Deno et al. ........................ 607/9 |

FOREIGN PATENT DOCUMENTS

| WO | WO2004047918 | 6/2004 |
| WO | WO2004080533 | 9/2004 |

* cited by examiner

*Primary Examiner* — Allen Porter, Jr.
(74) *Attorney, Agent, or Firm* — Reed A. Duthler; Stephen W. Bauer

(57) ABSTRACT

Refractory period stimulation (RPS) disclosed herein includes apparatus and methods to enhance cardiac performance by delivering monophasic stimulation pulses during the refractory period. The disclosure describes several system level improvements to RPS that include one or more of the following: (i) Delivery of RPS therapy pulses at multiple sites in an automatically alternating way to avoid increasing demand at any one location for prolonged periods of time. (ii) Delivery of RPS therapy pulses at multiple sites to determine one or more optimal electrode configurations for chronic RPS therapy delivery. (iii) Use of separate electrode(s) for sensing ventricular activity to properly time and adjust the application of RPS thereby avoiding limitations associated with electrode polarization that occurs due to the amount of energy delivered during the RPS. (iv) Use of a relatively long active recharge pulse at the RPS stimulation electrodes to remove the undesirable effects of polarization.

10 Claims, 6 Drawing Sheets

APPARATUS AND METHODS OF DELIVERING AN ENHANCED REFRACTORY PERIOD STIMULATION THERAPY

CROSS REFERENCE TO RELATED APPLICATIONS

This patent disclosure relates to two non-provisional patent applications filed on even date hereof; namely, application Ser. No. 11/379,892, filed Apr. 24, 2006, now U.S. Pat. No. 8,046,064 issued Oct. 25, 2011 by Deno and Warkentin entitled, "A METHOD OF DELIVERYING PESP/ICC AS WELL AS ADJUSTING THE REFRACTORY PERIOD OF THE HEART," and application Ser. No. 11/379,904, filed Apr. 24, 2006, now U.S. Pat. No. 7,835,789 issued Nov. 16, 2010 by Euler entitled, "REFRACTORY PERIOD STIMULATION TO INCREASE VENTRICULAR MECHANICAL PERFORMANCE," the contents of which are fully incorporated by reference herein.

FIELD OF THE INVENTION

The invention relates to cardiac pacing and, more particularly, to delivery of pulse trains of electrical stimulation therapy delivered to multiple sites within a cardiac chamber either during cardiac pacing therapy delivery or passive cardiac monitoring.

BACKGROUND OF THE INVENTION

Refractory period stimulation (RPS) therapy includes therapeutic electrical stimulation that when delivered to myocardial tissue does not trigger or evoke depolarization response from the surrounding myocardial tissue (i.e., does not trigger an electromechanical contraction of the heart). The stimulus does not trigger a mechanical contraction because the stimulus is delivered to the myocardial tissue during a period when the tissue is refractory. Myocardial tissue in an absolute refractory state cannot be captured regardless of the amount of electrical energy delivered thereto while such tissue in a relatively refractory state can be captured provided adequate energy delivery during a given pulse.

The inventor has discovered a particularly efficient enhanced RPS therapy delivery regimen that improves ventricular performance for heart failure patients.

SUMMARY

In general, the invention is directed to a medical device, such as an implantable pulse generator (IPG) that delivers stimulation to refractory myocardial tissue. The IPG delivers one or more monophasic stimulation pulses (nominally one to about six discrete pulses) to the myocardial tissue during periods when the tissue is absolutely or relatively refractory. Because monophasic stimulation therapy delivery tends to accumulate polarization on the active face of stimulation electrodes, one aspect of the invention involves delivery of an "active recharge" pulse following delivery of a pulse train.

The effects of such polarization were described in U.S. Pat. No. 4,406,286 to Stein which is incorporated herein and which is summarized hereinbelow in the context of traditional cardiac pacing therapy delivery (i.e., delivery of stimulus which the myocardium is non-refractory). The delivery of an electrical stimulus to cardiac tissue induces a field which is generally orders of magnitude greater in amplitude that the field caused by the electrical activity of the tissue itself. When the stimulus ends, electrical fields remain in tissue primarily due to two factors. The first factor relates to the electrochemical equilibrium at the electrode-tissue interfaces, which has been disturbed by the stimulus, and has to reestablish itself. The second factor relates to the function of the pacemaker's output capacitor being recharged through its electrical circuits, which involve the heart as well. When the same electrodes are used as pacing electrodes to stimulate myocardial contraction and as sensing electrodes to detect the resulting depolarization, detection of depolarization is typically somewhat reduced, because it is masked or buried in the exponential decay of the residual polarization charge on the electrode resulting from the stimulation pulse itself. U.S. Pat. No. 4,406,286 to Stein relates to a pacemaker having an R-wave capture detection capability in which the same electrodes are utilized for both pacing and sensing (i.e., unipolar or bipolar), and wherein a biphasic pulse is delivered for purposes of dissipating the polarization charge on the pacing electrode. According to Stein the first phase of a stimulus pulse is of relatively shorter duration and greater amplitude than the second phase for purposes of stimulating the myocardium, while the second phase is of relatively longer duration, lesser amplitude and opposite polarity than the first phase for purposes of providing charge compensation to neutralize the undesired electrode polarization, following which the capture detection sensing amplifier is turned on. Such "fast recharge" wave forms have been employed for many years in an attempt to facilitate short blanking and refractory time intervals following stimulation.

In contrast, in the context of the present invention wherein due to a plurality of discrete monophasic, non-capturing RPS pulses undesirable polarization effects can accumulate and cause corrosion of an electrode. Over a long enough period of time, the electrode could essentially disappear. This effect is suspected to involve ion migration from the exposed surfaces of an electrode used to delivery electrical stimulation to adjacent tissue. Thus, one aspect of the invention relates to implementing at least one active recharge pulse to the therapy delivery electrode(s) that are in contact with the myocardium during RPS therapy delivery. The active recharge can be implemented whether the monophasic pulse trains are delivered via bipolar electrodes (i.e., closely spaced electrodes in contact with myocardium) or via unipolar electrodes (i.e., one electrode in contact with myocardium and one spaced from the heart—typically coupled to the IPG housing). In this aspect of the invention, the active recharge pulse comprises relatively longer, lower amplitude of opposite polarity to the monophasic RPS therapy pulses. For example, if a bipolar (or unipolar) RPS pulse train having six discrete positive polarity eight volt (+8 V) pulses having five ms duration are delivered then an active recharge pulse could comprise a single negative polarity pulse of about two-tenths of a volt (−0.2 V) having on the order of about 100 ms duration. On the other hand, the duration could rise to as high as about 1200 ms. Such an active recharge technique can be implemented following: every delivery of an RPS pulse train, every individual pulse of the pulse train, a fractional or percentage of the delivered RPS pulse trains, receipt of a remote (via telemetry) triggering signal, N-cardiac cycles, a completed cycle of RPS therapy delivery, and the like.

In some embodiments, the IPG delivers the pulses during a period from approximately 30 to 200 ms (ms) subsequent to a detected depolarization of myocardial tissue. The stimulation pulses delivered by an IPG according to the invention are on the order of about 0.03 ms to about 1.6 ms with voltage amplitude of about 0.5 volts to about 8 volts. The amplitude of electrical current of the stimulation pulses can be I less than or equal to approximately 20 milliamps or other appropriate value. According to the invention an IPG delivers the pulses separated by a temporal interval of approximately 20 ms (i.e., 50 Hz). Furthermore, the pulses are delivered to multiple sites within at least one cardiac chamber—either the left ventricle (LV), right ventricle (RV)—or both ventricles of the heart. In some embodiments, the pulses are applied to the atria as well in order to enhance atrial contractility. In one embodiment two independent ventricular pacing/sensing medical electrical leads are deployed into communication with a portion of a RV. In another, a multiple electrode epicardial LV lead and a multiple electrode RV lead are deployed into operative communication with stimulation pulse circuitry of an IPG. In the latter embodiment, a bi-ventricular therapy can continue to be delivered (e.g., a cardiac resynchronization therapy, or CRT) with a one, all or a subset of the multiple electrodes operatively deployed for enhanced RPS therapy delivery.

Refractory period stimulation (RPS) according to the invention includes apparatus and methods to enhance cardiac performance via delivery of stimulation pulses during the refractory period. It is believed that such stimulation enhances myocyte performance in the region of stimulation, which leads to an overall improvement in cardiac function. This invention describes several system level improvements to RPS that include one or more of the following. Delivery of RPS therapy pulses at multiple sites in an automatically alternating way to avoid creating an increased demand in any one region of the heart for prolonged periods of time. Delivery of RPS therapy pulses at multiple sites to determine one or more optimal electrode configurations for chronic RPS therapy delivery. Use of separate electrode(s) for sensing ventricular activity to properly time and adjust the application of RPS thereby avoiding limitations associated with electrode polarization that occurs due to the amount of energy delivered during the RPS. Use of a relatively long active recharge pulse at the RPS stimulation electrodes to remove polarization. Use of a combination of alternating RPS delivery at one site with active recharge at a second site.

In some embodiments, an IPG delivers RPS pulses according to a schedule stored in a memory; for example, during certain periods of the day or upon command issued by a clinician or patient, or a detected increase in physiologic demand. Therapy delivery can be interrupted in the event of relatively high heart rates (relatively short P-P wave or R-R wave intervals) or upon detection of an arrhythmia. In such embodiments, the IPG suspends or withholds delivery of enhanced RPS therapy based on detection of such arrhythmias and rapid heart rate (e.g., tachycardia episodes, sinus tachycardia, etc.). Device performance and/or diagnostic information can be stored within a memory structure and reviewed to confirm delivery of a desired therapy regimen (e.g., using a so-called marker channel, or temporal cardiac activity strip and/or a percentage of time, or percentage of cardiac cycles) to track actual therapy delivery.

The details of one or more embodiments of the invention are set forth in the accompanying drawings and the description below. Other features, objects, and advantages of the invention will be apparent from the description and drawings, and from the claims.

DETAILED DESCRIPTION OF THE ILLUSTRATED EMBODIMENTS

Figure 1:
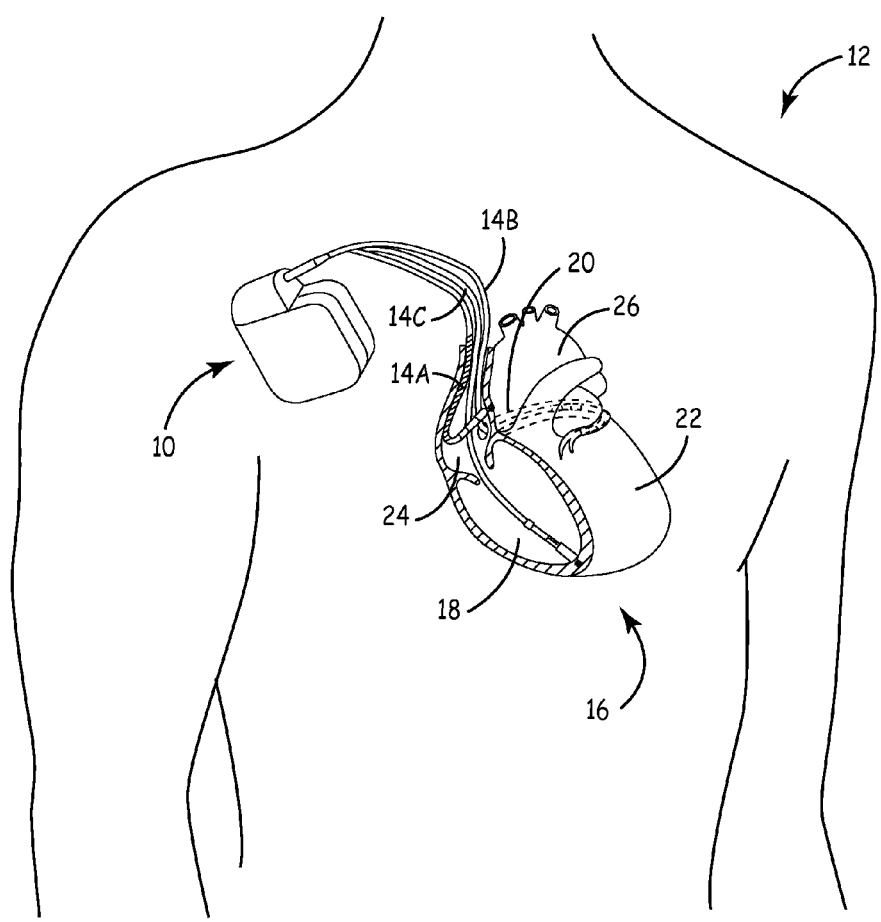
FIG. 1 is a conceptual diagram illustrating an exemplary IPG that delivers RPS pulses according to the invention implanted in a patient.

In the following detailed description, references are made to illustrative embodiments for methods and apparatus for delivering an enhanced RPS therapy regimen. The illustrated embodiments are not intended as exhaustive and should be viewed as merely describing certain aspects of the invention to those of skill in the art. Other embodiments having slight variation or modification from those illustrated herein are intended to fall within the scope of the claimed invention.

The present invention provides enhanced RPS therapy delivery in a multiple electrode IPG adapted to couple to multiple locations within a cardiac chamber or chambers. In one aspect, various stimulation vectors are used for RPS therapy delivery while one or more physiologic and/or metabolic sensors monitor or measure diverse cardiac performance metrics. The monitored or measured metrics are then compared and the relatively superior stimulation vector (or vectors) are used for chronic RPS therapy delivery. In another aspect the RPS therapy delivery electrodes used to deliver the RPS therapy regimen receive active recharge (polarization conditioning) from time to time to reduce latent polarization thereon. In yet another aspect RPS therapy and active recharge are alternatively delivered at two such that one site receives RPS and the other receives the active recharge.

FIG. 1A illustrate an exemplary implantable pulse generator (IPG) device 10 that delivers enhanced RPS pulse therapy to myocardial tissue according to the invention. In some embodiments, IPG 10 takes the form of a multi-chamber cardiac pacemaker. In the exemplary embodiment illustrated in FIG. 1A, IPG 10 is implanted in a patient 12, and is coupled to leads 14A, 14B and 14C (collectively "leads 14") that extend into the heart 16 of patient 12.

More particularly, RV lead 14A extends through one or more veins (not shown), the superior vena cava (not shown), and right atrium 24, and into RV 18. A LV (coronary sinus) lead 14B extends through the veins, the vena cava, right atrium 24, and into the coronary sinus 20 to a point adjacent to the free wall of LV 22 of heart 16. Right atrial (RA) lead 14C extends through the veins and vena cava, and into the right atrium 24 of heart 16.

Figure 2A:
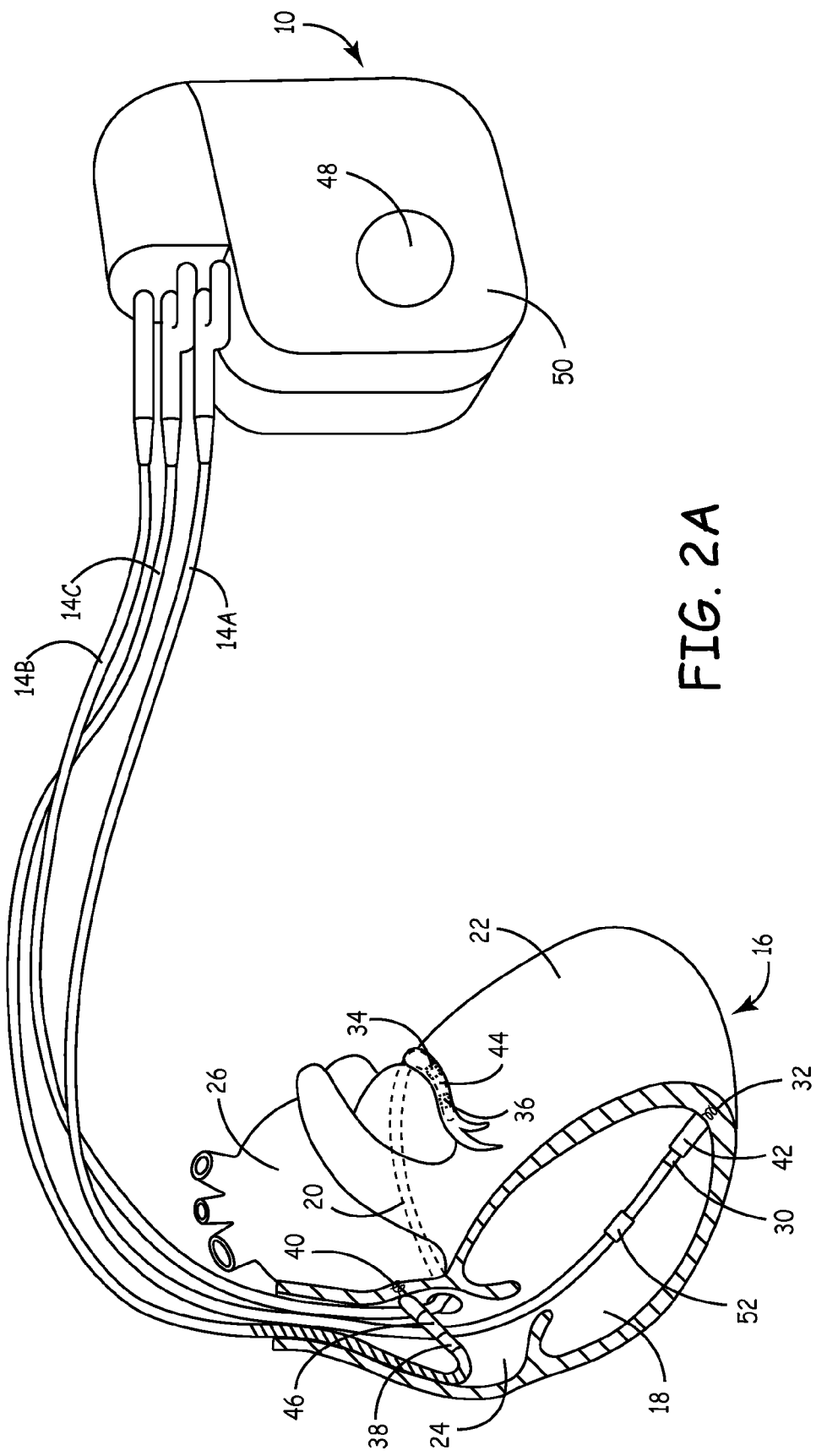
FIG. 2 is conceptual diagram further illustrating the IPG of FIG. 1 and the heart of the patient.
Figure 2B:
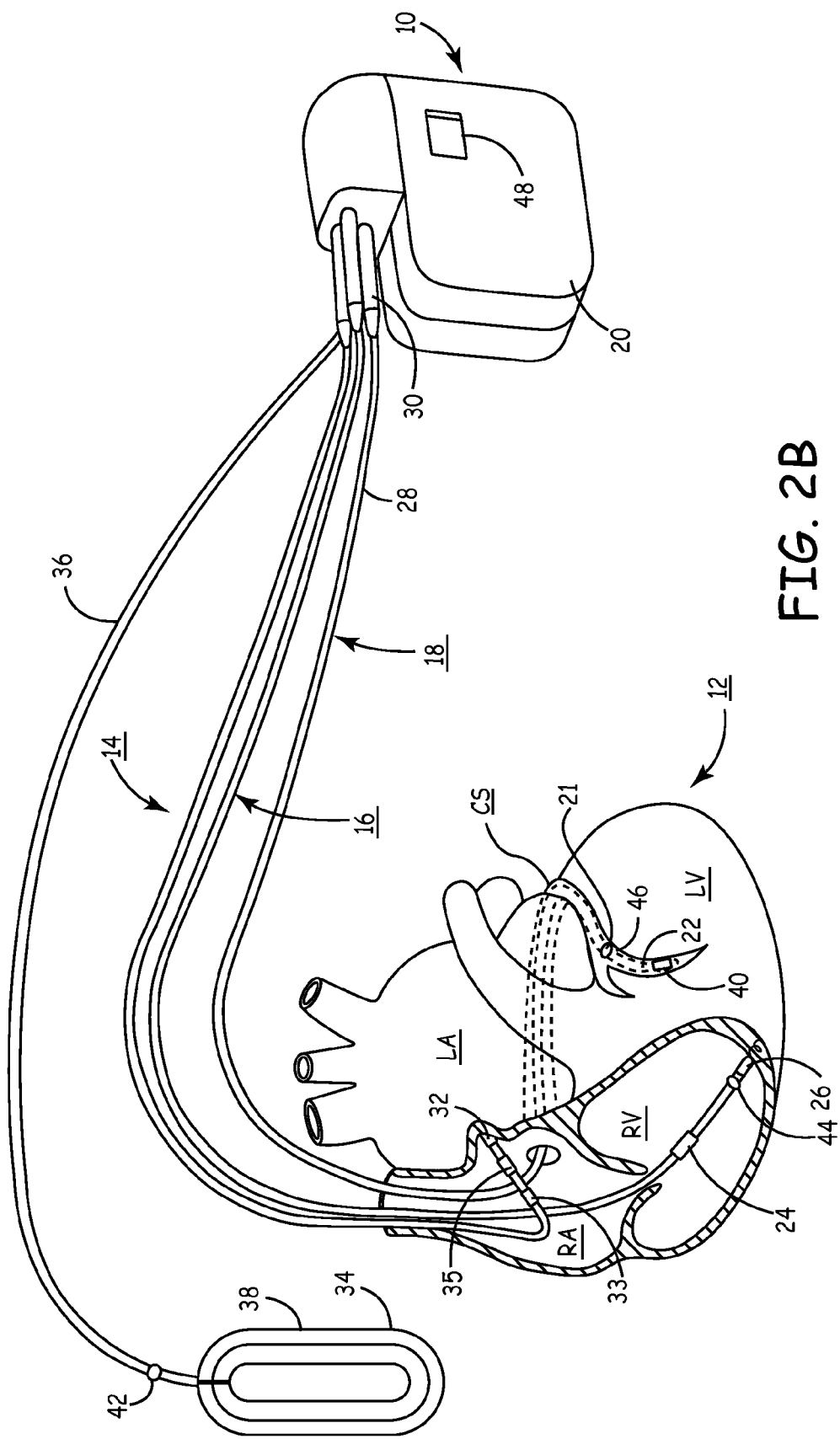

Each of leads 14 and/or IPG 10 includes electrodes and/or sensor units (e.g., see locations and structure—denoted by numerals 30, 32, 34, 36, 38, 40, 42, 44, 50 in FIG. 2A and numerals 21, 22, 24, 26, 32, 33, 35, 38, 44, 48 in FIG. 2B) used by IPG 10 to sense electrical signals and/or cardiac performance metrics attendant to the cyclic depolarization, contraction, repolarization, and relaxation of heart 16. The IPG 10 delivers RPS pulses to tissue of heart 16 at one or more locations via the electrodes located on one or more of leads 14. In some embodiments, IPG 10 also uses the electrodes located on one or more of leads 14 to deliver pacing pulses to and/or sense activity of heart 16 (i.e., delivers pulses intended to cause a depolarization and contraction of heart 16). For example, the illustrated multi-chamber IPG 10 can deliver pacing pulses to ventricles 18 and 22 via the electrodes located on leads 14A and 14B with an inter-ventricular delay therebetween to provide cardiac resynchronization therapy (CRT) to heart 16. The electrodes located on leads 14 can be unipolar, bipolar, or multi-electrode as is well known in the art.

IPG 10 delivers one or more RPS pulses to myocardial tissue of heart 16 during a period in which the tissue is refractory (e.g., when stimulation energy will not trigger tissue depolarization). In some embodiments the energy level of RPS pulses delivered by IPG 10 is similar to that of pacing pulses. In such embodiments, delivery of RPS pulses by IPG 10 does not significantly drain the battery (not shown) of IPG 10, and is unlikely to cause patient 12 to experience pain.

The configuration of IPG 10 and leads 14 illustrated in FIG. 1 is merely illustrative. In various embodiments, IPG 10 can couple to any number of leads 14 that extend to a variety of positions within, on or outside of heart 16. For example, in some embodiments, IPG 10 is coupled to a lead 14 that extends to left atrium 26 of heart 16, or epicardial leads 14 that extend to any position on an exterior surface of heart 16. Consequently, in various embodiments, IPG 10 is capable of delivering RPS pulses to myocardial tissue at any location within or outside of heart 16 via electrodes located on leads 14. Further, IPGs that deliver RPS pulses according to some embodiments of the invention are not implanted in patient 12, but instead are coupled to subcutaneous leads 14 that extend through the skin of patient 12 to a variety of positions within or outside of heart 16.

In one form of the invention diverse stimulation vectors between a pair of electrodes (e.g., electrode locations 21, 22, 24, 26, 32, 33, 35, 38, 44, 48 in FIG. 2B) are used for RPS therapy delivery while one or more metabolic and/or mechanical sensors (same reference numerals or different locations) monitor or measure cardiac performance metrics or parameters. The vector or vectors that produce relatively superior metrics or parameters are then used for chronic RPS therapy delivery. In a related form of the invention, the stimulation vectors are varied following delivery of one RPS therapy pulse train to a different vector for an entire subsequent RPS therapy pulse train. A further variation on this form involves varying the pulse train delivery vector for one or more discrete pulses of a single RPS pulse therapy train. For example, every other pulse of an RPS pulse train FIG. 2 is a conceptual diagram further illustrating IPG 10 and heart 16 of patient 12. In some embodiments, each of leads 14 includes an elongated insulative lead body carrying a number of concentric coiled conductors separated from one another by tubular insulative sheaths. In the illustrated embodiment, bipolar electrodes 30/32,34/36,38/40 are located adjacent distal end of the leads 14A,14B,14C, respectively. In exemplary embodiments, electrodes 30,34 and 38 may take the form of ring electrodes, and electrodes 32,36,40 take the form of extendable helix tip electrodes mounted retractably within insulative electrode heads 42,44,46, respectively. Each of the electrodes 30-40 is coupled to one of the coiled conductors within the lead body of its associated lead 14.

Sense/pace electrodes 30, 32, 34, 36, 38, 40 sense electrical signals attendant to the depolarization and repolarization of heart 16. The electrical signals are conducted to IPG 10 via leads 14. In some embodiments, as described above, IPG 10 delivers pacing pulses via one or more of the bipolar electrode pairs. In the illustrated embodiment, IPG 10 also includes an indifferent housing electrode 48, formed integrally with an outer surface of the hermetically sealed housing 50 of IPG 10. In such embodiments, IPG 10 is capable of using any of electrodes 30, 32, 34, 36, 38 and 40 for unipolar sensing or pacing in combination with housing electrode 48.

IPG 10 is capable of delivering RPS pulses via any combination of electrodes 30-40 and 48. In some embodiments, IPG 10 delivers defibrillation and/or cardioversion shocks to heart 16 via elongated coil defibrillation electrodes (not shown) carried on one or more of leads 14. In such embodiments, IPG is also capable of delivering RPS pulses via any of electrodes 30-40 in combination with one or more of these defibrillation electrodes.

In some embodiments, IPG 10 includes a sensor 52 that generates a signal as a function of a physiological parameter of patient 12, and delivers RPS pulses to tissue of heart 16 as a function of the physiological parameter. In exemplary embodiments, sensor 52 generates a signal as a function of a physiological parameter that reflects heart rate and/or the presence or absence of an arrhythmia, and IPG 10 monitors the signal to identify a need to inhibit enhanced RPS therapy delivery. In response to such a signal, IPG 10 halts delivery of RPS pulses. In the embodiment illustrated in FIG. 2, sensor 52 comprises an electrode pair for sensing heart rate and/or classifying arrhythmia episodes. Thus, sensor 52 could simply comprise a dedicated pair of electrodes or could in fact constitute a pair of pacing/sensing electrodes that were previously deployed for enhanced RPS therapy delivery.

Figure 3A:
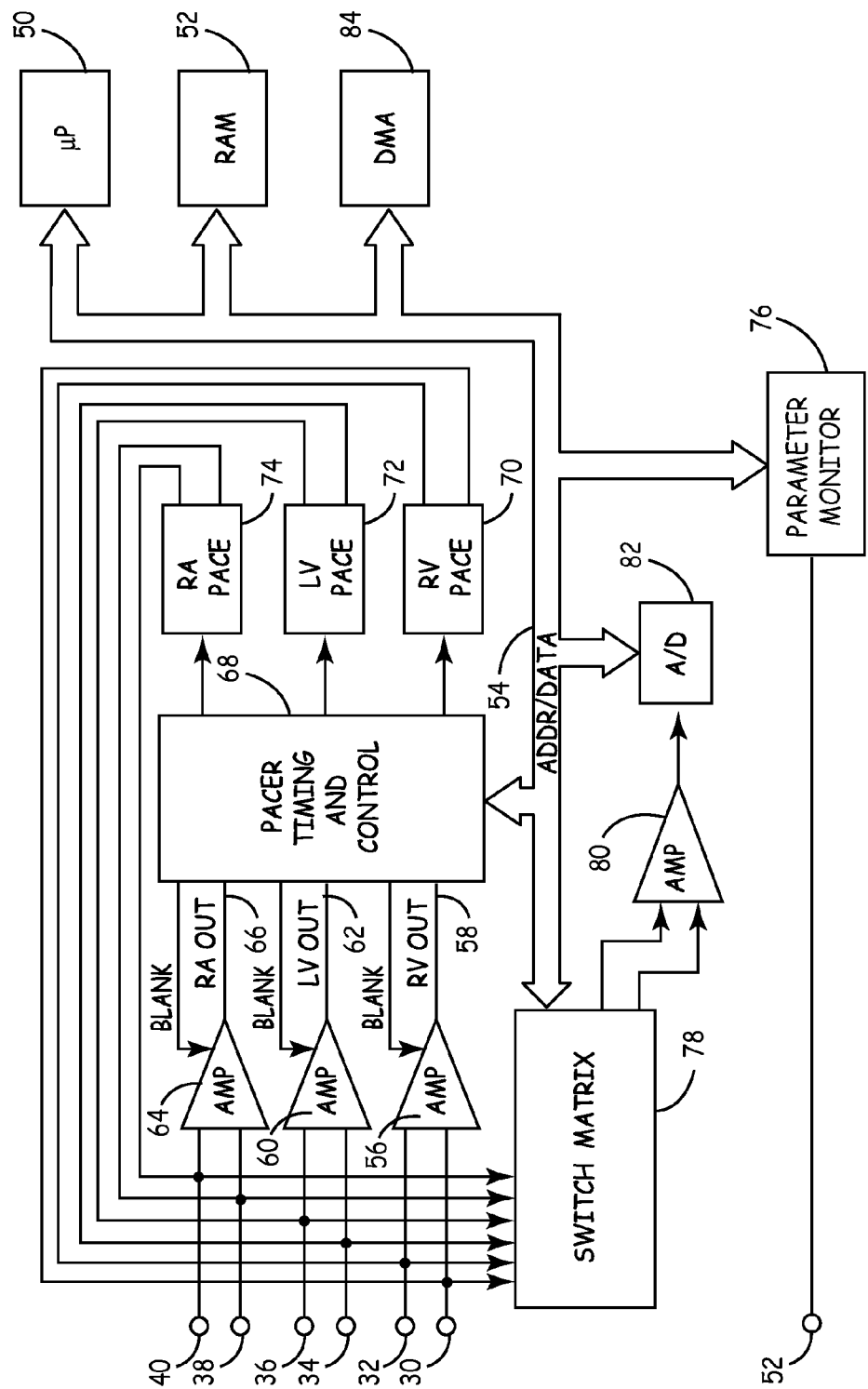
FIGS. 3A and 3B are functional block diagrams of an exemplary IPG adapted to deliver RPS therapy according to the invention.

FIG. 3A is a functional block diagram of IPG 10. In the illustrated embodiment, IPG 10 takes the form of a multi-chamber pacemaker having a microprocessor-based architecture. However, this diagram should be taken as exemplary of the type of device in which various embodiments of the present invention may be embodied, and not as limiting, as it is believed that the invention may be practiced in a wide variety of device implementations, including devices that are configured to only deliver enhanced RPS therapy, but do not provide cardiac pacing, cardioversion, and/or defibrillation therapies. Such an embodiment can include an IPG that merely monitors electrical cardiac activity and titrates enhanced RPS therapy delivery.

IPG 10 includes a microprocessor 50 configured to execute program instructions stored in a memory, e.g., a computer-readable medium, such as a ROM, EEPROM, flash memory, RAM 52, DRAM, and the like. Program instructions stored in a computer-readable medium and executed by the microprocessor 50 causes microprocessor 50 to perform the therapy delivery and interruption functions of the present invention. Microprocessor 50 couples to various other components of IPG 10 via an address/data bus 54 as is known in the art.

IPG 10 senses electrical activity within heart 16 via electrodes 30, 32 that are in turn coupled to amplifier 56, which can comprise an automatic gain controlled (AGC) amplifier providing an adjustable sensing threshold as a function of the measured R-wave amplitude. A signal is generated on RV out line 58 whenever the signal sensed between electrodes 30,32 exceeds the present sensing threshold. Thus, electrodes 30,32 and amplifier 56 are used to detect evoked and intrinsic RV depolarizations.

Electrodes 34, 36 are coupled to amplifier 60, which also takes the form of an AGC amplifier providing an adjustable sensing threshold as a function of measured R-wave amplitude. A signal is generated on LV out line 62 whenever the signal sensed between electrodes 34,36 exceeds the present sensing threshold. Thus, electrodes 34,36 and amplifier 60 are used to detect evoked and intrinsic LV depolarizations.

Electrodes 38, 40 are coupled to amplifier 64, which takes the form of an AGC amplifier providing an adjustable sensing threshold as a function of the measured P-wave amplitude. A signal is generated on RA out line 66 whenever the signal between electrodes 38,40 exceeds the present sensing threshold. Thus, electrodes 38,40 and amplifier 64 are used to detect evoked and intrinsic atrial depolarizations.

IPG 10 delivers RPS pulses to tissue of heart 16. Pacer timing/control circuitry 68 controls delivery of RPS pulses by one or more of output circuits 70-74 via electrodes 30, 40. Output circuits 70-74 include known circuitry for storage and delivery of energy in the form of pulses, such as switches, capacitors, and the like.

Pacer/timing and control circuitry 68 includes programmable digital counters that control the timing of delivery of RPS pulses. Pacer/timing control circuitry 68 further controls the width and amplitude of RPS pulses delivered by output circuits 70-74. Circuitry 68 controls the timing, width and amplitude of RPS pulses delivered by output circuits 70-74 based on information received from microprocessor 50 via data bus 54. The timing, width and amplitude of RPS pulses delivered by IPG 10 according to the invention will be described in greater detail below.

Microprocessor 50 controls the delivery of RPS pulses by IPG 10 by indicating to pacer/timing control circuitry 68 when RPS pulses are to be delivered, via which of electrodes 30-40 and 48 RPS pulses are to be delivered, and the timing, width and amplitude of RPS pulses to be delivered. In some embodiments, microprocessor 50 controls delivery of RPS pulses such that enhanced RPS therapy delivery occurs on a diurnal basis, upon patient activation, and/or for a preset duration. In some embodiments, microprocessor 50 enables delivery of RPS pulses according to a schedule stored in a memory, such as RAM 52, which indicates times of day or the like for delivery of RPS pulses.

In some embodiments, microprocessor 50 controls delivery of RPS pulses as a function of a physiological heart rate or presence of an arrhythmia condition parameter of a patient 12, as discussed above.

Although described herein in the context of a microprocessor-based pacemaker embodiment IPG 10, the invention may be embodied in various IPGs that include one or more processors, which may be microprocessors, DSPs, FPGAs, or other digital logic circuits. For example, IPG 10 may include analog slope or threshold detecting amplifier circuits to identify and measure the QT interval and/or ST segment within an electrogram signal, as is known in the art.

In some embodiments, IPG 10 paces heart 16. Pacer timing/control circuitry 78 includes programmable digital counters which control the basic time intervals associated with modes of pacing. Circuitry 78 also preferably controls escape intervals associated with pacing. For example, where IPG 10 paces right atrium 24, timing/control circuitry 78 triggers generation of pacing pulses by pacer output circuit 84, which is coupled to electrodes 38,40, upon expiration of an atrial escape interval.

IPG 10 can be configured to delivery bi-ventricular pacing therapy such as a CRT therapy. When delivering CRT, pacer timing/control circuitry 68 triggers generation of pacing pulses for one of ventricles 18,20 by the respective one of pacer output circuits 70,72 upon expiration of an A-V escape interval, and the other of ventricles 18,20 by the respective one of pacer output circuits 70,72 upon expiration of a V-V escape interval.

Pacer timing/control circuitry 68 resets escape interval counters upon detection of R-waves or P-waves, or generation of pacing pulses, and thereby controls the basic timing of cardiac pacing functions. Intervals defined by pacing circuitry 68 also include refractory periods during which sensed R-waves and P-waves are ineffective to restart timing of escape intervals, and the pulse widths of the pacing pulses. The durations of these intervals are determined by microprocessor 50 in response to data stored in RAM 52, and are communicated to circuitry 68 via address/data bus 54. Pacer timing/control circuitry 68 also determines the amplitude of the cardiac pacing pulses under control of microprocessor 50.

Microprocessor 50 operates as an interrupt driven device, and is responsive to interrupts from pacer timing/control circuitry 68 corresponding to the occurrence of sensed P-waves and R-waves and corresponding to the generation of cardiac pacing pulses. Those interrupts are provided via data/address bus 56. Any necessary mathematical calculations to be performed by microprocessor 50 and any updating of the values or intervals controlled by pacer timing/control circuitry 58 take place following such interrupts.

Figure 3B:
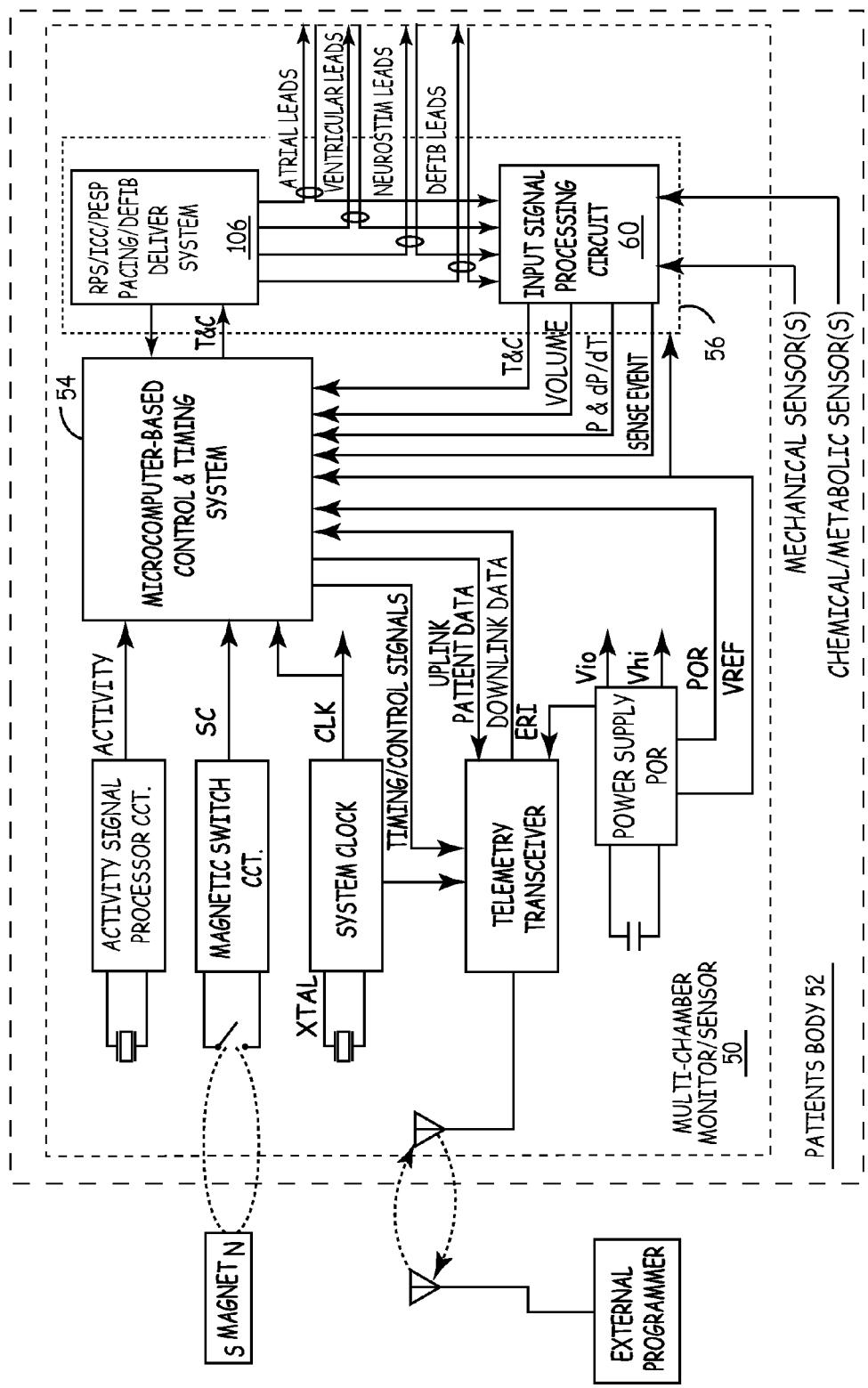

FIG. 3B depicts system architecture of exemplary multi-chamber monitor/sensor 50 implanted in a patient's body 52 which provides delivery of a therapy and/or physiologic input signal processing. As is known, the typical multi-chamber monitor/sensor 50 has a system architecture constructed about a microcomputer-based control and timing system 54 which varies in sophistication and complexity based on the type and functional features incorporated therein. The monitor/sensor 50 also typically includes patient interface circuitry 56 for receiving signals from sensors and/or pace/sense electrodes located at sites of the patient's heart chambers. In certain embodiments, the patient interface circuitry 56 is equipped to deliver RPS therapy to one or more of the heart chambers. As shown, patient interface circuitry 56 includes a RPS/PACING/DEFIB therapy delivery system 58, optionally including pacing and other stimulation therapies, and a physiologic input signal processing circuit 108 for processing the physiologic and/or metabolic signals (e.g., blood pressure, acceleration, volumetric signals, blood glucose) output by diverse sensors adapted to operatively couple to the heart. In certain embodiments, as shown, a set of lead connections are provided for making electrical connections between the therapy delivery system 58 and an input signal processing circuit 60 and sets of pace/sense electrodes located in operative relation to the RA, LA, RV and LV. Alternatively, in addition to the RPS therapy delivery aspects, a therapy delivery system 58 according to the invention can be configured as an implantable drug pump for delivering drugs into the heart (e.g., to alleviate symptoms of heart failure) or as an implantable heart assist device or pump (e.g., LV assist device, or LVAD) implanted in patients awaiting a heart transplant operation. As depicted in FIG. 3B, chemical/metabolic sensor input and/or mechanical sensor inputs are provided to the input signal processing circuit 60. As appreciated by those of skill in the art, a wide variety of such sensors may be utilized when practicing embodiments of the invention. In order for the exemplary circuit of FIG. 3B to implement RPS, pacing or cardiac defibrillation therapy accordingly, the therapy delivery system 58 needs to utilize appropriate circuitry. For example, if an RPS therapy delivery electrode is disposed remotely from the heart, the delivery of therapy may occur independent of the cardiac cycle (e.g., periodically approximately between 10 ms and about 10 seconds). While many different types of pulses may be employed for therapy delivery. Effective RPS therapy may be delivered using a variety of electrode configurations (e.g., between one and several discrete electrodes). Also, standard tip, ring, coil, can, and subcutaneous electrodes may be utilized to effectively deliver RPS therapy. While not specifically depicted in the drawings, suitable external circuitry may be adapted for therapy delivery including use of surface electrode patches, pads or paddles as well as pericardial electrodes. In particular, one or more electrodes disposed in the pericardial sac will be well positioned to stimulate cardiac tissue according to the invention. The physiologic input signal processing circuit 60 includes at least one electrical signal amplifier circuit for amplifying, processing, and in some cases, detecting sense events from the electrical sense signal or sensor output signal. The physiologic input signal processing circuit 60 in multi-chamber monitor/sensors providing dual chamber, multi-site, or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 54 for sampling, digitizing, and storing or transmitting in an uplink transmission. Atrial and ventricular sense amplifiers include signal processing stages for respectively detecting the occurrence of a P-wave or R-wave and providing an A-SENSE or V-SENSE event signal to the control and timing system 54. The timing and control system 54 responds in accordance with its operating system to deliver or modify a pacing therapy, if appropriate, or to accumulate data for uplink telemetry transmission or to provide a Marker Channel® signal in a variety of ways known in the art. In addition, the input signal processing circuit 108 includes at least one physiologic sensor signal-processing channel for sensing and processing a sensor-derived signal from a physiologic sensor located in relation to a heart chamber or elsewhere in the body.

Figure 4:
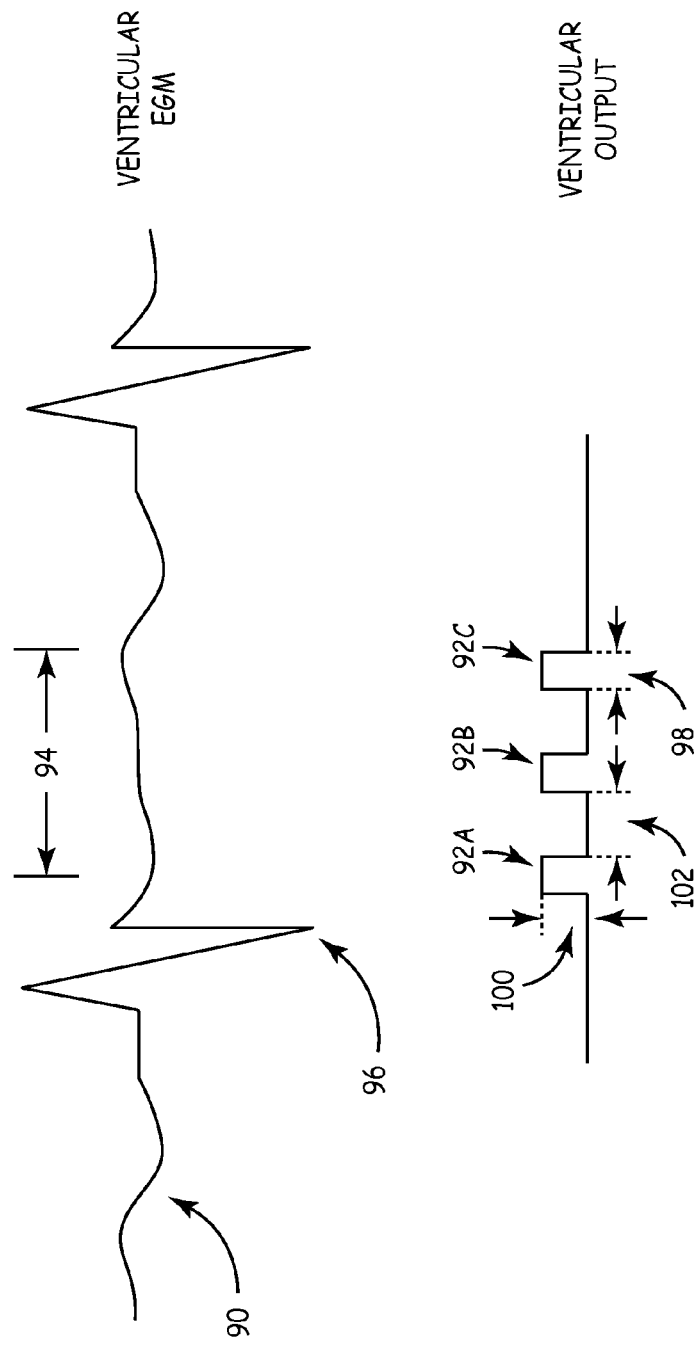
FIG. 4 is a timing diagram illustrating an example electrogram and exemplary RPS pulses.

FIG. 4 is a timing diagram illustrating an example electrogram signal 90 and exemplary RPS pulses 92A-C (collectively "RPS pulses 92) delivered by IPG 10 according to an embodiment of the invention. In the illustrated example, electrogram signal 90 is a ventricular electrogram signal, e.g., a signal detected via one of leads 14A and 14B. Further, as illustrated in FIG. 4, RPS pulses 92 are delivered to one of ventricles 18,22 via one of leads 14A,14B.

IPG 10 delivers RPS pulses 92 to tissue in heart 16 during a period 94 when the tissue is refractory. When directed to control delivery of RPS pulses by microprocessor 50, pacer timing/control circuitry 68 detects occurrence of an R-wave 96 in the manner described above with reference to FIGS. 3A and 3B, and delivers RPS pulses during period 94 subsequent to R-wave 96 when tissue is refractory. In exemplary embodiments, circuitry 68 controls delivery of RPS pulses during a period 94 that extends from forty to eighty ms after detection of R-wave 96 to ensure that the tissue is refractory and that RPS pulses 92 are delivered prior to a second depolarization of the tissue. Where RPS pulses 92 are delivered to tissue of one of atria 24,26, refractory period 94 may be determined based on detection of a P-wave by circuitry 68 in the manner described above.

As indicated above, in exemplary embodiments the energy level of a pulse 92 of the pulse train consists of about: a pulse width of about 0.03 ms to about 1.6 ms; a current amplitude 100 of each pulse 92 is less than or equal to approximately twenty milliamps; a voltage amplitude is between about 0.5 volts and about 8 volts; and the pulse train is delivered at about 50 Hz (i.e., 20 ms separation between pulses).

Although illustrated as having the same width 98 and amplitude 100, pacer timing/control circuitry 68 can deliver each of pulses 92 with different widths 98 and amplitudes 100.

Pacer timing/control circuitry 68 controls delivery of one or more RPS pulses 92 during refractory period 94 including a programmable blanking period of about 50 ms and 300 ms following delivery of the last pulse in a given pulse train. The blanking period allows the electrodes to recover from polarization effects following delivery of a pulse train. A pulse train begins to be delivered from about 30 ms to about 200 ms following detection of a paced or intrinsic depolarization.

In the example illustrated in FIG. 4, circuitry 68 controls delivery of a train of three pulses 92A-C during refractory period 94. In exemplary embodiments, circuitry 68 controls delivery of pulse trains that include six of fewer RPS pulses 92 during refractory period 94.

Circuitry 68 controls delivery of pulses 92 such that they are separated by an interval 102. In exemplary embodiments, interval 102 is less than or equal to about 20 ms (50 Hz). Although illustrated as separated by a constant interval 102, in some embodiments, pulses 92 are separated by intervals 102 that vary from pulse-to-pulse and/or from pulse train to pulse train.

In accordance with an aspect of the present invention, methods and apparatus are provided efficient, programmable methods and apparatus for delivering a enhanced RPS therapy to one or more chambers of a heart. Single chamber and multiple chamber embodiments of the invention include endocardial and epicardial electrodes locations and permit the continued simultaneous delivery of a CRT or other pacing regimen. Diagnostics included within the context of the invention include arrhythmia detection algorithms that, upon confirmation of an arrthymia episode, interrupt enhanced RPS therapy delivery and provide temporal records of actual therapy delivery (percentage time, percentage cardiac cycles, etc.). In addition, enhanced RPS therapy delivery will be interrupted according to the invention in the event that a relatively high heart rate is detected.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of delivering a refractory period stimulation (RPS) therapy, comprising:
   delivering, during a single cardiac cycle, between one and six successive cardiac refractory period stimulation (RPS) pulses during a refractory period of a cardiac chamber,
   wherein said delivered RPS pulses occur between a first pair of electrodes, said first pair of electrodes defining a first stimulation vector,
   wherein said successive pulses are separated by approximately 10 milliseconds (ms) and about 20 ms,
   wherein each said pulse has a pulse duration of between 0.03 ms and 1.6 ms and wherein each said pulse has a voltage amplitude of between 0.5 volts and 8.0 volts;
   delivering, during a subsequent cardiac cycle following said single cardiac cycle, a new set of RPS pulses between a second pair of electrodes defining a second stimulation vector;
   interrupting delivery of the RPS pulses in the event that one of a supra-threshold heart rate is detected and an arrhythmia condition is detected;
   monitoring a physiologic signal from one of a mechanical cardiac sensor and a metabolic sensor wherein said sensor operatively couples to the cardiac chamber and provides a first output signal correlated to the first stimulation vector and a second output signal correlated to the second stimulation vector; and determining an enhanced RPS therapy delivery vector based at least in part upon a parameter of the first output signal and the second output signal.

2. A method according to claim 1, further comprising: chronically delivering an enhanced RPS therapy between the pair of electrodes that corresponds to the enhanced RPS therapy delivery vector.

3. A method according to claim 1, wherein the mechanical cardiac sensor comprises one of:
an accelerometer, an intracardiac pressure transducer, a blood flow sensor; and
wherein the metabolic sensor comprises one of: a optical-type oxygen sensor, a lactate sensor, a CO2 sensor, a potassium sensor, a calcium sensor, a thrombin sensor, a c-reactive protein sensor, a glucose sensor.

4. An apparatus adapted to delivery a refractory period stimulation (RPS) therapy, comprising:
means for delivering, during a single cardiac cycle, between one and six successive monophasic cardiac refractory period stimulation (RPS) pulses during a refractory period of a cardiac chamber, said RPS pulses comprising a first set of RPS pulses,
wherein said first set of RPS pulses are delivered between a first pair of electrodes, said pair of electrodes defining a first stimulation vector, wherein said successive pulses are separated by approximately 10 milliseconds (ms) and about 20 ms, wherein each said pulse has a pulse duration of between 0.03 ms and 1.6 ms and wherein each said pulse has a voltage amplitude of between 0.5 volts and 8.0 volts;
means for delivering, during a subsequent cardiac cycle following said single cardiac cycle, a new set of RPS pulses between a second pair of electrodes defining a second stimulation vector;
means for interrupting delivery of both the first set and the second set of RPS pulses in the event that one of a supra-threshold heart rate is detected and an arrhythmia condition is detected;
means for monitoring a physiologic signal from one of a mechanical cardiac sensor and a metabolic sensor wherein said sensor operatively couples to the cardiac chamber and provides a first output signal correlated to the first stimulation vector and a second output signal correlated to the second stimulation vector; and
means for determining an enhanced RPS therapy delivery vector based at least in part upon a parameter of the first output signal and the second output signal.

5. An apparatus according to claim 4, further comprising:
means for chronically delivering an enhanced RPS therapy between the pair of electrodes that corresponds to the enhanced RPS therapy delivery vector.

6. An apparatus according to claim 4, wherein the mechanical cardiac sensor comprises one of: an accelerometer, an intracardiac pressure transducer, a blood flow sensor; and
wherein the metabolic sensor comprises one of: a optical-type oxygen sensor, a lactate sensor, a CO2 sensor, a potassium sensor, a calcium sensor, a thrombin sensor, a c-reactive protein sensor.

7. A method of delivering a refractory period stimulation (RPS) therapy, comprising:
during a first cardiac cycle, delivering one or more cardiac refractory period stimulation (RPS) pulses to a cardiac chamber between a first pair of electrodes, during a refractory period of the cardiac chamber;
during a second cardiac cycle following said first cardiac cycle, delivering a new set of RPS pulses to a cardiac chamber between a second pair of electrodes; and interrupting delivery of the RPS pulses in the event that one of a supra-threshold heart rate is detected and an arrhythmia condition is detected;
monitoring a physiologic signal from one of a mechanical cardiac sensor and a metabolic sensor wherein said sensor operatively couples to the cardiac chamber and provides a first output signal correlated to and a second output signal correlated to delivery of the RPS pulses between the second pair of electrodes; and
responsive to the first and second signals, selecting one of said first and second pairs of electrodes for chronic delivery of RPS pulses thereafter.

8. An apparatus adapted to delivery a refractory period stimulation (RPS) therapy, comprising:
means for delivering, during a first cardiac cycle, one or more cardiac refractory period stimulation (RPS) pulses to a cardiac chamber between a first pair of electrodes, during a refractory period of the cardiac chamber;
means for delivering, during a second cardiac cycle following said first cardiac cycle, delivering a new set of RPS pulses to a cardiac chamber between a second pair of electrodes; and
means for interrupting delivery of both the first set and the second set of RPS pulses in the event that one of a supra-threshold heart rate is detected and an arrhythmia condition is detected;
means for monitoring a physiologic signal from one of a mechanical cardiac sensor and a metabolic sensor wherein said sensor operatively couples to the cardiac chamber and provides a first output signal correlated to and a second output signal correlated to delivery of the RPS pulses between the second pair of electrodes; and
means responsive to the first and second signals, for selecting one of said first and second pairs of electrodes for chronic delivery of RPS pulses thereafter.

9. A method of delivering a refractory period stimulation (RPS) therapy, comprising:
during a first cardiac cycle, delivering one or more cardiac refractory period stimulation (RPS) pulses to a cardiac chamber between a first pair of electrodes, during a refractory period of the cardiac chamber;
during a second cardiac cycle following said first cardiac cycle, delivering a new set of RPS pulses to a cardiac chamber between a second pair of electrodes;
monitoring a physiologic signal from one of a mechanical cardiac sensor and a metabolic sensor wherein said sensor operatively couples to the cardiac chamber and provides a first output signal correlated to and a second output signal correlated to delivery of the RPS pulses between the second pair of electrodes; and
responsive to the first and second signals, selecting one of said first and second pairs of electrodes for chronic delivery of RPS pulses thereafter.

10. An apparatus for delivering a refractory period stimulation (RPS) therapy, comprising:
means for delivering, during a first cardiac cycle, one or more cardiac refractory period stimulation (RPS) pulses to a cardiac chamber between a first pair of electrodes, during a refractory period of the cardiac chamber;
means for delivering, during a second cardiac cycle following said first cardiac cycle, delivering a new set of RPS pulses to a cardiac chamber between a second pair of electrodes;
means for monitoring a physiologic signal from one of a mechanical cardiac sensor and a metabolic sensor wherein said sensor operatively couples to the cardiac chamber and provides a first output signal correlated to and a second output signal correlated to delivery of the RPS pulses between the second pair of electrodes; and means responsive to the first and second signals, for selecting one of said first and second pairs of electrodes for chronic delivery of RPS pulses thereafter.

* * * * *